Figure 1:
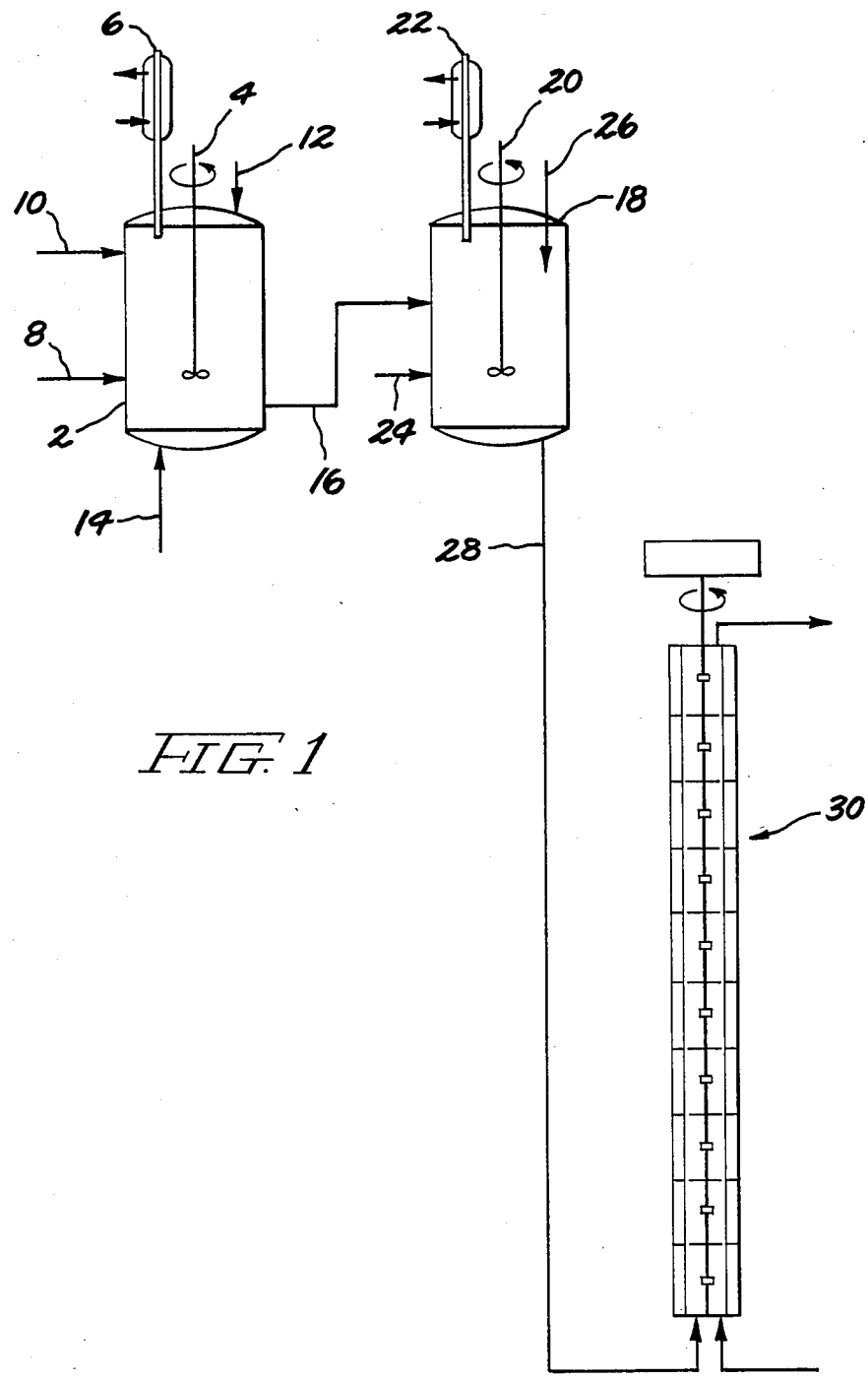

United States Patent [19]

Silva et al.

[11] Patent Number: 4,737,573

[45] Date of Patent: Apr. 12, 1988

[54] METHOD FOR POLYMERIZING AROMATIC BISCHLOROFORMATE COMPOSITION TO POLYCARBONATE

[75] Inventors: James M. Silva, Clifton Park, N.Y.; Robert A. Pyles, Evansville, Ind.

[73] Assignee: General Electric Company, Schenectady, N.Y.

[21] Appl. No.: 917,751

[22] Filed: Oct. 10, 1986

[51] Int. Cl.[4] .............................................. C08G 63/62
[52] U.S. Cl. ..................................... 528/371; 528/198; 528/199; 528/370
[58] Field of Search ................ 528/371, 370, 198, 199

[56] References Cited

U.S. PATENT DOCUMENTS

| | | | |
|---|---|---|---|
| 3,189,640 | 6/1965 | Dietrich et al. | 260/463 |
| 3,269,985 | 8/1966 | Loncrini | 528/371 |
| 3,646,102 | 2/1972 | Kobayashi et al. | 260/463 |
| 3,959,335 | 5/1976 | Vernaleken et al. | 260/463 |
| 3,966,785 | 6/1976 | Krimm et al. | 260/463 |
| 4,025,489 | 5/1977 | Bailey et al. | 260/47 X A |
| 4,089,888 | 5/1978 | Tokumitsu et al. | 260/463 |
| 4,122,112 | 10/1978 | Koda et al. | 260/463 |

FOREIGN PATENT DOCUMENTS

86/03192  6/1986  PCT Int'l Appl. .

Primary Examiner—Harold D. Anderson
Attorney, Agent, or Firm—William H. Pittman; James C. Davis, Jr.; James Magee, Jr.

[57] ABSTRACT

Bischloroformate oligomer compositions are prepared by passing phosgene into a heterogeneous aqueous-organic mixture containing at least one dihydroxyaromatic compound, with simultaneous introduction of a base at a rate to maintain a specific pH range and to produce a specific volume ratio of aqueous to organic phase. By this method, it is possible to employ a minimum amount of phosgene. The reaction may be conducted batchwise or continuously. The bischloroformate composition may be employed for the preparation of cyclic polycarbonate oligomers or linear polycarbonate, and linear polycarbonate formation may be integrated with bischloroformate composition formation in a batch or continuous process.

10 Claims, 2 Drawing Sheets

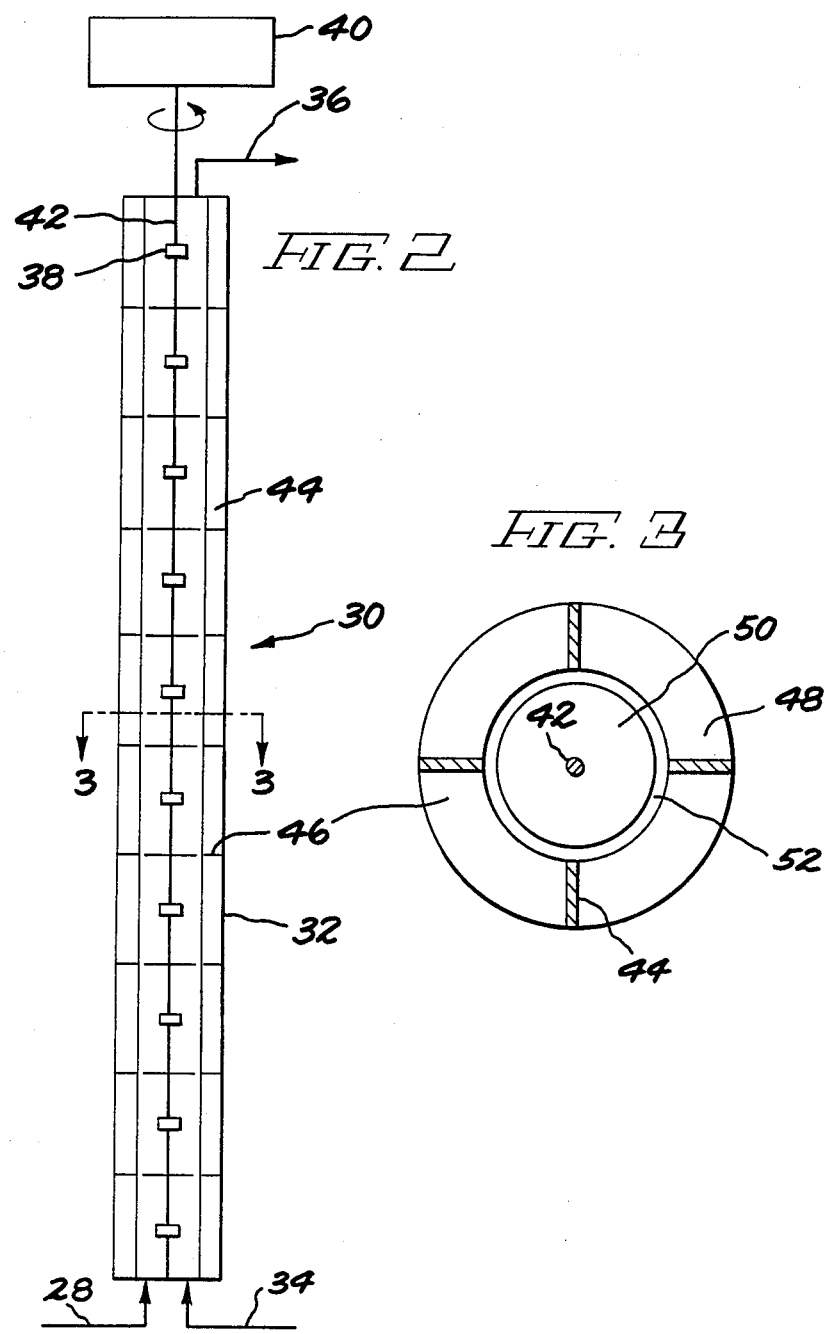

METHOD FOR POLYMERIZING AROMATIC BISCHLOROFORMATE COMPOSITION TO POLYCARBONATE

This invention relates to the preparation of bischloroformate compositions convertible to linear polycarbonates and cyclic polycarbonate oligomers. More particularly, it relates to the preparation of such oligomer compositions in conventional equipment widely used for polycarbonate production.

The preparation of bischloroformate oligomer compositions and their conversion to linear polycarbonates is known. Reference is made, for example, to U.S. Pat. Nos. 3,646,102, 4,089,888 and 4,122,112. It is also known from European patent application No. 162,379 and copending, commonly owned application Ser. No. 704,122, filed Feb. 22, 1985, now U.S. Pat. No. 4,644,053, that crude bischloroformate compositions containing oligomers can be converted to cyclic polycarbonate oligomers, which are versatile intermediates for linear polycarbonates.

A principal advantage in the preparation of linear polycarbonates from bischloroformate oligomer compositions is the relative purity of the products. This is particularly true when the molecular weight of the polycarbonate is regulated by the use of an endcapping agent such as phenol, t-butylphenol or p-cumylphenol. The use of such endcapping agents in reaction mixtures utilizing phosgene causes the formation of diaryl carbonates such as diphenyl carbonate as by-products.

It has been found that the presence of such diaryl carbonates may cause difficulties in molding operations. These may include problems in removing molded polycarbonate articles from the mold, in producing parts using rapid cycle times, and in producing parts without physically or optically flawed surfaces. Such problems can be particularly vexatious when regularity of shape of such molded articles is a prime concern, such as in the molding of optical disks. By the use of bischloroformate oligomers, formation of monomeric carbonates and the attendant problems are avoided.

The above-listed patents describe various methods of preparing bischloroformate oligomers in tube reactors. Such methods are of value when reactors of this type are available. However, it is often preferred to equip polycarbonate manufacturing facilities with more conventional and versatile units such as stirred tank reactors. Moreover, it may be desirable to use such equipment for both conventional polycarbonate preparation from phosgene (when the presence of monomeric carbonates is not detrimental) and polycarbonate preparation from bischloroformate oligomers. More particularly, it would be desirable to prepare bischloroformate oligomers in a sequence of operations which can be integrated with their conversion either to linear polycarbonates or to cyclic polycarbonate oligomer compositions.

By the present invention, a convenient method for preparation of bischloroformate oligomer compositions is provided. Said method employs readily available, conventional equipment and may be conveniently integrated with the preparation of linear polycarbonates or cyclic polycarbonate oligomers. Moreover, the method produces bischloroformate oligomer compositions of relatively low average molecular weight, which are relatively stable, free from large amounts of high polymer and are readily convertible to either end product as desired. Also provided is a method for preparing linear polycarbonates employing said bischloroformate oligomer compositions as intermediates.

Accordingly, one aspect of the present invention is a method for preparing an aromatic bischloroformate composition which comprises passing phosgene into a heterogeneous mixture consisting essentially of water, a substantially inert, substantially water-insoluble organic liquid and at least one dihydroxyaromatic compound in a tank reactor, and simultaneously introducing an aqueous alkali or alkaline earth metal base solution at a rate to maintain the aqueous phase of said mixture at a pH in the range of 8–11; the temperature of said mixture being maintained in the range of about 15°–50° C., the volume ratio of aqueous to organic phase at the conclusion of phosgenation being in the range of about 0.4–1.0:1 and the total amount of phosgene employed being at least about 1.1 mole per mole of dihydroxyaromatic compound; said mixture being agitated under conditions at least sufficient to prevent segregation of the aqueous and organic liquid phases.

The bischloroformate compositions prepared by the method of this invention comprise mixtures of compounds of varying molecular weight, said compounds having the formula

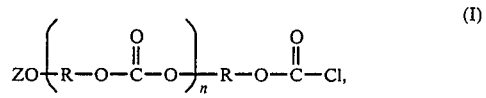

wherein R is a divalent aromatic radical, Z is hydrogen or

and n is 0 or a positive number. When the composition is to be converted to linear polycarbonate, it may contain substantial proportions of monochloroformate (Z is hydrogen). For cyclics formation, however, the proportion of monochloroformate should be minimized and the invention permits such minimization. It is also often desirable to maximize the proportion of bischloroformates in which n is from 0 to about 6, at the expense of higher bischloroformates, unreacted dihydroxyaromatic compounds and other by-products.

These bischloroformate compositions are prepared from dihydroxyaromatic compounds having the formula HO-R-OH. The R values may be aromatic hydrocarbon or substituted aromatic hydrocarbon radicals, with illustrative substituents being alkyl, cycloalkyl, alkenyl (e.g., crosslinkable-graftable moieties such as allyl), halo (especially fluoro, chloro and/or bromo), nitro and alkoxy.

The preferred R values have the formula $$-A^1-Y-A^2-, \quad (II)$$

wherein each of $A^1$ and $A^2$ is a monocyclic divalent aromatic radical and Y is a bridging radical in which one or two atoms separate $A^1$ from $A^2$. The free valence bonds in formula II are usually in the meta or para positions of $A^1$ and $A^2$ in relation to Y.

In formula II, the $A^1$ and $A^2$ values may be unsubstituted phenylene or substituted derivatives thereof wherein the substituents are as defined for R. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated $C_{1-12}$ aliphatic or alicyclic radical such as methylene, cyclohexylmethylene, [2.2.1]bicycloheptylmethylene, ethylene, ethylidene, 2,2-propylidene, 1,1-(2,2-dimethylpropylidene), cyclohexylidene, cyclopentadecylidene, cyclododecylidene or 2,2-adamantylidene, especially an alkylidene radical. Aryl-substituted radicals are included, as are unsaturated radicals and radicals containing atoms other than carbon and hydrogen; e.g., oxy groups. Substituents such as those previously enumerated may be present on the aliphatic, alicyclic and aromatic portions of the Y group.

For the most part, the suitable compounds include biphenols and especially bisphenols. Frequent reference will be made to bisphenols hereinafter, but it should be understood that other compounds equivalent thereto may be employed as appropriate.

The following dihydroxyaromatic compounds are illustrative:
Resorcinol
4-Bromoresorcinol
Hydroquinone
4,4'-Dihydroxybiphenyl
1,6-Dihydroxynaphthalene
2,6-Dihydroxynaphthalene
Bis(4-hydroxyphenyl)methane
Bis(4-hydroxyphenyl)diphenylmethane
Bis(4-hydroxyphenyl)-1-naphthylmethane
1,1-Bis(4-hydroxyphenyl)ethane
1,2-Bis(4-hydroxyphenyl)ethane
1,1-Bis(4-hydroxyphenyl)-1-phenylethane
2,2-Bis(4-hydroxyphenyl)propane ("bisphenol A")
2-(4-Hydroxyphenyl)-2-)3-hydroxyphenyl) propane
2,2-Bis(4-hydroxyphenyl)butane
1,1-Bis(4-hydroxyphenyl)isobutane
1,1-Bis(4-hydroxyphenyl)cyclohexane
1,1-Bis(4-hydroxyphenyl)cyclododecane
Trans-2,3-bis(4-hydroxyphenyl)-2-butene
2,2-Bis(4-hydroxyphenyl)adamantane
α,α'-Bis(4-hydroxyphenyl)toluene
Bis(4-hydroxyphenyl)acetonitrile
2,2-Bis(3-methyl-4-hydroxyphenyl)propane
2,2-Bis(3-ethyl-4-hydroxyphenyl)propane
2,2-Bis(3-n-propyl-4-hydroxyphenyl)propane
2,2-Bis(3-isopropyl-4-hydroxyphenyl)propane
2,2-Bis(3-sec-butyl-4-hydroxyphenyl)propane
2,2-Bis(3-t-butyl-4-hydroxyphenyl)propane
2,2-Bis(3-cyclohexyl-4-hydroxyphenyl)propane
2,2-Bis(3-allyl-4-hydroxyphenyl)propane
2,2-Bis(3-methoxy-4-hydroxyphenyl)propane
2,2-Bis(3,5-dimethyl-4-hydroxyphenyl)propane
2,2-Bis(2,3,5,6-tetramethyl-4-hydroxyphenyl)propane
2,2-Bis(3-5-dichloro-4-hydroxyphenyl)propane
2,2-Bis(3,5-dibromo-4-hydroxyphenyl)propane
2,2-Bis(2,6-dibromo-3,5-dimethyl-4-hydroxyphenyl)-propane
α,α-Bis(4-hydroxyphenyl)toluene
α,α,α',α'-Tetramethyl-α,α'-bis(4-hydroxyphenyl)-p-xylene
2,2-Bis(4-hydroxyphenyl)hexafluoropropane
1,1-Dichloro-2,2-bis(4-hydroxyphenyl)ethylene
1,1-Dibromo-2,2-bis(4-hydroxyphenyl)ethylene
1,1-Dichloro-2,2-bis(5-phenoxy-4-hydroxyphenyl)ethylene
4,4'-Dihydroxybenzophenone
3,3-Bis(4-hydroxyphenyl)-2-butanone
1,6-Bis(4-hydroxyphenyl)-1,6-hexanedione
Ethylene glycol bis(4-hydroxyphenyl) ether
Bis(4-hydroxyphenyl) ether
Bis(4-hydroxyphenyl) sulfide
Bis(4-hydroxyphenyl) sulfoxide
Bis(4-hydroxyphenyl) sulfone
Bis(3,5-dimethyl-4-hydroxyphenyl) sulfone
9,9-Bis(4-hydroxyphenyl)fluorene
2,7-Dihydroxypyrene
6,6'-Dihydroxy-3,3,3',3'-tetramethylspiro(bis)indane ("spirobiindane bisphenol")
3,3-Bis(4-hydroxyphenyl)phthalide
2,6-Dihydroxydibenzo-p-dioxin
2,6-Dihydroxythianthrene
2,7-Dihydroxyphenoxathiin
2,7-Dihydroxy-9,10-dimethylphenazine
3,6-Dihydroxydibenzofuran
3,6-Dihydroxydibenzothiophene
2,7-Dihydroxycarbazole.

The preferred dihydroxyaromatic compounds are those which are substantially insoluble in aqueous systems at temperatures within the range of 20°–40° C. and pH values in the range of about 1–5. Thus, dihydroxyaromatic compounds of relatively low molecular weight and high solubility in water, such as resorcinol and hydroquinone, are generally less preferred. Bisphenol A (in which Y is isopropylidene and $A^1$ and $A^2$ are each p-phenylene) is often especially preferred for reasons of availability and particular suitability for the purposes of the invention.

Also useful are bisphenols containing ester linkages. These may be prepared, for example, by reacting two moles of bisphenol A with one mole of isophthaloyl or terephthaloyl chloride.

Phosgene, water and at least one substantially inert organic liquid are also employed in the method of this invention. The solubility of the bisphenol in the organic liquid is usually up to about 0.25 M at temperatures in the range of about 20°–40° C., and preferably up to about 0.1 M. Said organic liquid should generally also be substantially insoluble in water. Illustrative liquids are aliphatic hydrocarbons such as hexane and n-heptane; chlorinated aliphatic hydrocarbons such as methylene chloride, chloroform, carbon tetrachloride, dichloroethane, trichloroethane, tetrachloroethane, dichloropropane and 1,2-dichloroethylene; aromatic hydrocarbons such as benzene, toluene and xylene; substituted aromatic hydrocarbons such as chlorobenzene, o-dichlorobenzene, the chlorotoluenes, nitrobenzene and acetophenone; and carbon disulfide. The chlorinated aliphatic hydrocarbons, especially methylene chloride, are preferred.

Also employed is an aqueous alkali or alkaline earth metal base solution. It is most often a hydroxide such as sodium hydroxide, potassium hydroxide or calcium hydroxide. Sodium and potassium hydroxides, and especially sodium hydroxide, are preferred because of their relative availability and low cost. Frequent reference to sodium will be made hereinafter in this context, but the invention is obviously not limited thereto. The concentration of said solution is not critical and may be about 0.2–19 M.

According to the present invention, the bischloroformate-forming reaction is conducted in a tank reactor. Such reactors include continuous-flow stirred tank reactors (hereinafter "CSTR's"), which are particularly useful when the reaction is conducted continuously as described hereinafter.

Initially present in the reactor are a mixture consisting essentially of the water, organic liquid and bisphenol or at least a portion thereof, and phosgene and the base are subsequently introduced. Among the critical factors are the pH of the aqueous phase of the mixture and the volume ratio of aqueous to organic phase. These may be controlled by controlling the volume of water initially present and the rate of addition of base.

The pH of the aqueous phase should be in the range of 8–11. The identity of the reactive bisphenol species is believed to vary with the ambient pH. Below about 8.5, it is free bisphenol, and in the range of about 8.5–10 the monoanion becomes an increasingly important factor.

At still higher values the dianion, which is the most reactive species, appears. However, above about 11.2 the principal reaction is conversion to the dianion, which requires the addition of much additional base without being accompanied by a substantial increase in pH, until all of said bisphenol has been converted. Therefore, a pH above about 11 can result in wastage of base. High pH conditions may also occasionally be accompanied by fouling of equipment, especially pH monitoring means, with a tenacious coating of solid material. On the other hand, at pH levels of 8.5 or lower it is frequently found that a substantial proportion of the product is monochloroformate rather than bischloroformate; therefore, relatively high pH levels within the above-prescribed range should be used if the product is to be converted to cyclics. Balancing these factors, a pH in the range of 8.5–10.5 is generally preferred.

The necessity for pH control is a chief reason for conducting the reaction in a tank reactor. If a tube reactor were used, the alternatives for reagent addition would be introduction of base at intervals over the length of the tube, which is not very practical, and introduction of base with the other reagents at the end of the tube, whereupon the pH would continuously decrease with reagent flow through the tube. In addition, tank reactors are frequently standard equipment for polycarbonate production and one of the advantages of the invention is the use of conventional equipment.

The volume ratio of aqueous to organic phase at the conclusion of phosgenation should be in the range of about 0.4–1.0:1. Below about 0.4:1, it is frequently found that portions of the reaction system such as the pH sensing means become fouled with solids. This also tends to happen at ratios in the range of about 0.4–0.5:1, and as a consequence pH readings may be inaccurate. Therefore, the preferred ratio is about 0.5–1.0:1. Above 1:1., there may be excessive hydrolysis of phosgene or bischloroformates.

Reaction temperatures in the range of about 15°–50° C. are employed. Below 15° C. the rate of reaction may become too slow for convenience, while above 50° C. it becomes difficult to maintain a sufficient concentration of dissolved phosgene for efficiency. If the preferred organic liquid, methylene chloride, is used, the reaction may be conducted at reflux which is on the order of 35°–42° C. The reaction pressure is usually atmospheric, although sub- or superatmospheric pressures may be employed if desired.

In the tank reactor, heat removal and temperature control may be achieved by means of a simple condenser. This is another advantage over the use of a tube reactor, which requires elaborate cooling coils or equivalent control means. Such means may also be employed with a tank reactor when appropriate, however.

It is usually advantageous to adjust the phosgene addition rate in accordance with the pH level maintained in the reaction mixture. At high pH levels, excessive hydrolysis of phosgene and product may occur if said rate is too slow. Lower pH levels are more tolerant of variations in phosgene addition rate. In general, rapid phosgenation is advantageous since it results in formation in major proportion of lower molecular weight oligomers. The proper rate of addition can readily be determined by simple experimentation.

During the reaction, the mixture is agitated at a rate at least sufficient to prevent segregation of the aqueous and organic liquid phases. If segregation occurs, the reaction may be incomplete. There is no real upper agitation limit, although excessively rapid agitation may waste phosgene by increasing the hydrolysis rate thereof.

Under the above-described conditions, it is possible to achieve substantially complete conversion of the bisphenol to bischloroformate oligomers by employing a total of about 1.1–3.0 moles of phosgene per mole of bisphenol. If the molar ratio is higher than 3:1, the excess is wasted. Complete bisphenol dissolution is frequently noted at a ratio of 1.13:1, in which case any additional phosgene may serve only to ensure that reaction is complete.

The bischloroformate preparation method of this invention is adaptable to continuous operation. For this purpose, a CSTR may be employed. Said CSTR originally contains a portion of the water, organic liquid and bisphenol, with the remainder of each being added concurrently with the phosgene and base to maintain parameters in the above-described ranges.

For the most part, a reaction or residence time on the order of about 10–60 minutes is adequate for substantially complete conversion of bisphenol to bischloroformate composition. Following completion of the reaction, it is frequently advantageous to remove any unreacted phosgene so as to insure the absence of diaryl carbonates during subsequent polymerization. This may be achieved, for example, by purging the reaction mixture with an inert gas such as nitrogen, by continuing addition of base to selectively hydrolyze unreacted phosgene, or by a combination of these two operations. In batch processes, phosgene removal may be effected in the reaction vessel; in continuous processes, a second vessel downstream from the first may be used.

Removal of the aqueous phase at this point, followed if desired by washing of the organic phase free of inorganic by-products, are often preferred also. This is especially true when the bischloroformate composition is to be converted to linear polycarbonate, since such conversion is relatively sensitive to purity of the aqueous phase.

The distributions of the molecular species in the bischloroformate compositions prepared by the method of this invention may be determined by reversed phase high pressure liquid-liquid chromatography. The composition is first reacted with an equimolar mixture of phenol and triethylamine to produce the corresponding phenyl esters, which are resistant to hydrolysis under chromatography conditions. The phenyl esters are dissolved in a mixture of tetrahydrofuran and water and chromatographed using a relatively non-polar packing, whereupon lower molecular weight constituents are eluted first. For each molecular species, two values are determined and used for identification: the retention time (in minutes) and the area under the ultraviolet absorption peak at 254 nm., which is uniquely identifiable for compounds of this type.

The standards used for assignment of retention time and 254 nm. absorption are separately prepared linear compounds including bisphenol A mono- and diphenyl carbonate and the diphenyl carbonate of bisphenol A dimer. Higher oligomers are detected by analogy.

It is possible to isolate the bischloroformate composition prepared by the method of this invention by conventional means such as vacuum stripping of solvent. However, said composition is more often used directly, without isolation, as described hereinafter.

As previously mentioned, the bischloroformate oligomer compositions of this invention may be converted to cyclic polycarbonate oligomers and to linear polycarbonates. They may also be converted to polyester-polycarbonates by methods such as the one disclosed in U.S. Pat. No. 4,569,984.

For the preparation of cyclic polycarbonate oligomers, the bischloroformate oligomer composition, or a mixture thereof with at least one bisphenol or an alkali metal salt thereof, is contacted with at least one oleophilic aliphatic or heterocyclic tertiary amine (i.e., one which is soluble in and highly active in organic media, especially those used in the oligomer preparation method of this invention), and an aqueous alkali or alkaline earth metal hydroxide or carbonate solution, said contact being effected under conditions whereby bischloroformate is maintained in low concentration in a substantially non-polar organic liquid which forms a two-phase system with water. When such bisphenols (or their alkali metal salts) are present, they generally comprise up to about 50%, most often up to about 20% and preferably up to about 10%, of the bischloroformate-bisphenol combination. Most preferably, a bischloroformate composition alone or a mixture thereof with a bisphenol is used, as noted hereinafter.

The tertiary amines useful for cyclic oligomer preparation ("tertiary" in this context denoting the absence of N-H bonds) generally comprise those which are oleophilic and more particularly those which are useful for the formation of polycarbonates. Reference is made, for example, to the tertiary amines disclosed in U.S. Pat. Nos. 4,217,438 and 4,368,315, the disclosures of which are incorporated by reference herein. They include aliphatic amines such as triethylamine, tri-n-propylamine, diethyl-n-propylamine and tri-n-butylamine and highly nucleophilic heterocyclic amines such as 4-dimethylaminopyridine (which, for the purposes of this invention, contains only one active amine group). The preferred amines are those which dissolve preferentially in the organic phase of the reaction system; that is, for which the organic-aqueous partition coefficient is greater than 1. This is true because intimate contact between the amine and bischloroformate composition is essential for the formation of the cyclic oligomer mixture. For the most part, such amines contain at least about 6 and preferably about 6–14 carbon atoms.

The most useful amines are trialkylamines containing no branching on the carbon atoms in the 1- and 2-positions. Especially preferred are tri-n-alkylamines in which the alkyl groups contain up to about 4 carbon atoms. Triethylamine is most preferred by reason of its particular availability, low cost, and effectiveness in the preparation of products containing low percentages of linear oligomers and high polymers.

Suitable aqueous alkali or alkaline earth metal hydroxide or carbonate solutions (hereinafter sometimes designated "metal base solution") include lithium, sodium, potassium or calcium hydroxide or sodium or potassium carbonate. Lithium, sodium or potassium hydroxide are most often used, with sodium hydroxide being preferred because of its availability and relatively low cost. The concentration of the solution is not critical and may be about 0.2–16 M.

The fourth essential component in the cyclic oligomer preparation method is a substantially non-polar organic liquid which forms a two-phase system with water. The liquids described hereinabove with reference to preparation of the bischloroformate composition are suitable, with the same preferences.

To prepare the cyclic oligomer composition, the reagents and components are maintained in contact under conditions whereby the bischloroformate or bischloroformate-bisphenol composition is present in low concentration. Actual high dilution conditions, requiring a large proportion of organic liquid, may be employed but are usually not preferred for cost and convenience reasons. Instead, simulated high dilution conditions known to those skilled in the art may be employed. For example, in one embodiment of the method the bischloroformate composition (and optionally other reagents) are added gradually to a reaction vessel containing solvent. Although addition of bischloroformate composition neat (i.e., without solvents) is within the scope of this embodiment, it is frequently preferred to add it as a solution in the organic liquid, as described hereinabove. The proportion of organic liquid used for this purpose is not critical; about 25–75% by weight, and especially about 40–60%, is preferred.

The reaction temperature is generally in the range of about 0°–50° C. It is most often about 0°–40° C. and preferably 20°–40° C.

For maximization of the yield and purity of cyclic oligomers as opposed to high polymer and insoluble and/or intractable by-products, it is preferred to use not more than about 1.5 mole of bischloroformate or bischloroformate-bisphenol composition per liter of organic liquid in the reaction system, including any liquid used to dissolve said composition. Preferably, about 0.003–1.0 mole/liter of said composition is used when it consists entirely of bischloroformates, and no more than about 0.5 mole/liter when it is a mixture of bischloroformates and bisphenol or salt thereof. It should be noted that this is not a molar concentration in the organic liquid when said composition is added gradually, since the latter is consumed as it is added to the reaction system.

The molar proportions of the reagents constitute another important feature for yield and purity maximization. The preferred molar ratio of amine to bischloroformate composition used alone is about 0.1–1.0:1 and most often about 0.15–0.6:1, and that of metal base solution to said composition is about 1.5–3:1 and most often about 2–3:1. When a bischloroformate-bisphenol (or salt thereof) combination is used, the preferred molar ratio for amine is about 0.1–0.5:1 and for metal base solution is the same as above, including any hydroxide used to form a bisphenol salt.

The use of bisphenol alkali metal salt is of particular value when it is desired to minimize the amount of phosgene required for overall production of cyclic polycarbonates. When bischloroformate composition alone is used, half the phosgene used for bischloroformate formation is lost by hydrolysis upon conversion of the bischloroformate to cyclics. On the other hand, each chloroformate moiety can theoretically react with a bisphenol salt moiety to form a carbonate group if the latter is present in sufficient amount.

In practice, it is generally found that incorporation of bisphenol salt into cyclics under these conditions is incomplete. Thus, removal of any unreacted bisphenol as its alkali metal salt is usually necessary.

A highly preferred method for preparing the cyclic oligomer mixture comprises conducting the reaction using at least one aliphatic or heterocyclic tertiary amine which, under the reaction conditions, dissolves preferentially in the organic phase of the reaction system, and gradually adding the bischloroformate or bischloroformate-bisphenol composition and at least a portion of the amine and metal base solution simultaneously to the organic liquid or to a mixture thereof with water, said liquid or mixture being maintained at a temperature in the range of about 0°–50° C.; the amount of bischloroformate or bischloroformate-bisphenol composition used being up to about 0.7 mole for each liter of organic liquid present in the reaction system, and the total molar proportions of amine and metal base solution to said composition being approximately as follows:

Amine—0.06–2.0:1;
Metal base solution—2–3:1;

and recovering the cyclic oligomers thus formed.

A factor of some importance in this embodiment is the concentration of available amine, which should be maintained at a level as constant as possible during the entire addition period for bischloroformate composition. If all of the amine is present in the reaction vessel into which said composition is introduced, its concentration steadily decreases, principally by dilution. On the other hand, if amine is introduced continuously or in equal increments during introduction of said composition, its available concentration is initially low and increases more or less steadily during the addition period. These fluctuations can result in a high and constantly varying proportion of high polymer in the product.

When bisphenol or its salt is employed in this embodiment, cyclics yield is usually optimized if said reagent is absent from the portion of said composition added near the end of the reaction. In other words, it is often preferred that any batch be terminated by a period of addition of bischloroformate composition alone.

It has been found advantageous to introduce amine in one initial large portion, usually about 40–95% and preferably about 40–75% by weight of the total amount, followed by incremental or continuous addition of the balance thereof. By this procedure, the concentration of available amine is maintained at a fairly constant level in the organic phase during the entire addition period, and it is possible to minimize the proportion of high polymer in the product. Typically, high polymer content is 10% or less when this mode of addition is used.

Under these conditions, it is usually advantageous for the reaction vessel to initially contain about 5–40% and preferably about 5–30% of total metal base solution. The balance thereof is also introduced continuously or incrementally. As in the embodiment previously described, another portion of organic liquid may serve as a solvent for the bischloroformate composition.

Among the other principal advantages of this preferred embodiment are the non-criticality of the degree of dilution of the reagents and the ability to complete the addition and reaction in a relatively short time, regardless of reaction scale. It ordinarily takes only about 25–30 minutes to complete cyclic oligomer preparation by this method, and the cyclic oligomer yield may be 85–90% or more. By contrast, use of a less preferred embodiment may, depending on reaction scale, require an addition period as long as 8–10 hours and the crude product may contain substantial proportions of linear by-products with molecular weights of about 4,000-10,000, which, if not removed, may interfere with subsequent polymerization of the cyclic oligomers by acting as chain transfer agents.

In this preferred embodiment, the pH of the reaction mixture is typically in the range of about 9-14 and preferably about 12.

Any unwanted impurities, including high polymer (i.e., linear polycarbonate having a degree of polymerization greater than about 30), may be removed from the cyclic oligomers in the necessary amounts by conventional operations such as combining the crude product, as a solid or in solution, with a non-solvent for said impurities. Illustrative non-solvents include ketones such as acetone and methyl isobutyl ketone and esters such as methyl acetate and ethyl acetate. Acetone is a particularly preferred non-solvent.

Recovery of the cyclic oligomers normally means merely separating the same from diluent (by known methods such as vacuum evaporation) and, optionally, from high polymer and other impurities. The degree of sophistication of recovery will depend on such variables as the intended end use of the product.

An advantage in using bischloroformate oligomer compositions, rather than bisphenol bischloroformate, for the preparation of cyclic oligomers is a decrease in overall consumption of phosgene. Since each molecule of bisphenol reacts with two molecules of phosgene to form bischloroformate and one of those is lost upon oligomer formation and/or cyclization, there is a total wastage of 50% of the phosgene used. The same is true when a bischloroformate oligomer composition is employed, but 1.5 or less total molecules of phosgene have been employed for the preparation of said composition, and consequently, less is wasted. This advantage, coupled with the possibility of using bischloroformate oligomers for either cyclics or linear polycarbonate production as needed, more than outweigh the disadvantage of a somewhat greater percentage of high polymer in the cyclic oligomer product.

For the preparation of linear polycarbonates, the bischloroformate compositions prepared by the method of this invention may be condensed interfacially by contact with an interfacial polycarbonate formation catalyst and an acid acceptor, according to general methods known in the art. The interfacial reaction is typically conducted in a water-organic liquid mixture, suitable organic liquids being those described hereinabove and especially methylene chloride. The catalyst may be one of the above-described tertiary amines, especially triethylamine, or a quaternary ammonium or phosphonium salt or amidine of the type known in the art to be effective in the reaction of phosgene with bisphenols. The acid acceptor is typically an alkali or alkaline earth metal base of the type which has also been previously described. In general, the reaction may be conducted at a temperature in the range of about 0°-100° C. and preferably about 25°-50° C.; at a pH in excess of about 10, most often in the range of about 10-14 and preferably about 11-12.5; and using an amount of catalyst within the range of about 0.025-3.0 mole percent based on total bischloroformate. Also present in the reaction mixture may be at least one bisphenol or salt thereof, as previously described with reference to cyclic oligomer formation.

It has been found particularly advantageous to prepare polycarbonates from the bischloroformate compositions by a procedure which utilizes at least one tank reactor of the type previously described. Accordingly, another aspect of the invention is a method for preparing a linear polycarbonate which comprises the steps of:

(A) preparing a bischloroformate oligomer composition by the procedure described hereinabove;

(B) passing an interfacial polycarbonate formation catalyst into a mixture of said bischloroformate composition, water and a substantially inert, substantially water-insoluble organic liquid in a tank reactor, with effective agitation, and simultaneously introducing an aqueous alkali or alkaline earth metal base solution at a rate to maintain the aqueous phase of said mixture at a pH in the range of about 10-14, the rate of catalyst addition being adjusted to effect polycarbonate formation under controlled conditions; and (C) recovering said linear polycarbonate.

The linear polycarbonate preparation method of this invention may be conducted either batchwise or continuously. When conducted batchwise, it is frequently convenient to employ the same tank reactor in steps A and B. The aqueous phase of the step A product may be removed prior to commencement of step B, or both phases may remain in the reactor. In general, sufficient water is added to maintain a somewhat higher volume ratio of aqueous to organic phase in step B than in step A, said ratio most often being in the range of about 0.8-1.5:1.

The interfacial polycarbonate formation catalyst is passed into the mixture at a rate to effect controlled conversion to polycarbonate. Suitable rates can readily be determined by simple experimentation. Most often, the addition time thereof is about 1-20 minutes, with about 5-10 minutes being preferred. Aqueous base is simultaneously added to maintain an alkaline pH, most often in the range of about 10-12.5.

It is also within the scope of the invention to employ an effective amount of a monohydroxyaromatic compound (such as the previously described phenol, t-butylphenol or p-cumylphenol) to regulate molecular weight of the polycarbonate. The molecular weight regulator may be passed into the reaction mixture in the same manner as the bischloroformate condensation catalyst, frequently in admixture therewith, or it may be introduced prior to said catalyst. The amount thereof depends on the desired molecular weight and molecular weight distribution of the product, and is most often about 1-10 mole percent based on structural units in the bischloroformate composition.

When the organic liquid used is the preferred methylene chloride or has a boiling point similar thereto, step B is conveniently conducted at reflux. Under normal conditions, the reaction time required for a batch is about 20-40 minutes.

Step C, the recovery of the linear polycarbonate, may be achieved by conventional operations such as precipitation by a non-solvent, evaporation of solvent and/or filtration. The resulting aqueous phase may be discarded, or it may be recycled to step A since bischloroformate preparation is generally not as sensitive to water purity as polycarbonate preparation.

When linear polycarbonate preparation is conducted continuously, two CSTR's are employed in series, with step A being conducted in the first and step B in the second. A suitable vessel for removal of phosgene and, optionally, the aqueous phase may be placed between the two CSTR's. The solution of bischloroformate composition, catalyst or combination of catalyst and molecular weight regulator, and aqueous base are ordinarily introduced separately into the second CSTR, and the solution of the product linear polycarbonate in the organic liquid is continuously removed therefrom, usually in combination with an aqueous phase.

Under these conditions, it may be found that the conversion of bischloroformate to linear polycarbonate in the second CSTR is incomplete. If so, a further reaction system may be employed to increase the molecular weight thereof, with further addition of base as necessary for pH control. This further reaction system should ordinarily operate under limited back-mixing conditions; that is, under conditions which approach plug flow. The term "plug flow" is defined in Levenspiel, *Chemical Reaction Engineering*, Second Edition, p. 97, as follows:

> It is characterized by the fact that the flow of fluid through the reactor is orderly with no element of fluid overtaking or mixing with any other element ahead or behind. Actually, there may be lateral mixing of fluid in a plug flow reactor; however, there must be no mixing or diffusion along the flow path.

Thus, "limited back-mixing" in the present context means that there is little or, ideally, no mixing of high molecular weight with lower molecular weight polycarbonate. Limited back-mixing reaction systems include multiple CSTR's in series and continuous-flow tubular reactors, especially those in which baffles, packing, multiple reaction zones or the like are present to minimize flow in the reverse direction.

A typical limited back-mixing reactor used according to the present invention is divided into multiple reaction zones by horizontal baffles which restrict the flow of fluid from one zone to a preceding zone. Such a reactor is frequently referred to hereinafter as a "multi-zone reactor". One skilled in the art will recognize that the degree of back-mixing in such a reactor can be controlled by such design variables as the number of zones and the cross-sectional area of the horizontal baffles with respect to the cross-sectional area of the column. Typically the multi-zone reactor is an upright cylindrical vessel. Each stage is preferably agitated to provide efficient mixing, typically by turbine agitators. However, other mixing methods can be used such as reciprocating plate agitators, static mixers and the like. Either co-current or countercurrent flow of polycarbonate solution and aqueous base may be employed; for countercurrent flow, agitation is usually required.

The number of zones in the multi-zone reactor will obviously be greater than one, since one zone would be equivalent to a CSTR. As one skilled in the art will appreciate, more zones provide more limited back-mixing. It is currently believed that at least two zones will be necessary to achieve any significant limitation of back-mixing, and at least five zones are preferred. The number of zones will generally be set by process economics since increasing the number of zones will increase the cost of the reactor. Practically speaking, a reactor with more than 50 zones is unlikely, and usually about 5-20 zones are acceptable.

The temperature in the further reaction system is ordinarily somewhat lower than that in the CSTR, since the principal reaction is the condensation of large oligomers to make high molecular weight polymer and the number of reactions per unit time is relatively low. Typical temperatures are within the range of about 20°-35° C. It is also frequently found that relatively small quantities of base are needed in said further reaction system.

A further advantage of the linear polycarbonate formation method of this invention is that it permits close control of the overall conversion of bisphenol to polycarbonate. This is true because splitting the overall conversion into two segments, the first being bischloroformate oligomer production and the second being further polymerization, facilitates temperature and pH control by relatively simple means.

Reference is now made to the drawings in which FIG. 1 represents a reaction system suitable for use to prepare linear polycarbonates according to the present invention, FIG. 2 is a schematic diagram of a multi-zone limited back-mixing reactor useful as a further reaction system as described hereinabove, and FIG. 3 is a cross-sectional view of one stage of said reactor along the line 3—3 of FIG. 2.

As shown in FIG. 1, CSTR 2 is a bischloroformate preparation vessel provided with agitation means 4, typically a paddle agitator, condenser 6 and nitrogen purge means (not shown). Bisphenol, methylene chloride, aqueous sodium hydroxide solution and phosgene are continuously introduced at 8, 10, 12 and 14, respectively, the latter by suitable sparging means, while the mixture is agitated. Temperature control is achieved by maintaining the system at reflux.

The overflow from CSTR 2 is passed via line 16 to an optional phosgene and water removal vessel (not shown) and thence to a second CSTR 18, fitted with stirring means 20, condenser 22 and optional nitrogen purge means (not shown). Interfacial polycarbonate formation catalyst and molecular weight regulator are introduced as a methylene chloride solution at 24, and aqueous sodium hydroxide solution (preferably in relatively pure water) at 26.

The effluent from CSTR 18 is typically a linear polycarbonate which can be further reacted to increase molecular weight. It is passed via line 28 to the lower end of limited back-mixing reactor 30, said reactor being shown in more detail in FIG. 2.

Reactor 30 as shown in FIG. 2 has ten zones, one of which is designated as 32 and shown in cross-section in FIG. 3. The organic phase from CSTR 2 enters via line 28 and aqueous sodium hydroxide solution is introduced cocurrently as needed via line 34 (countercurrent addition may also be employed).

Centered in each zone is a turbine agitator 38; all such agitators are driven by motor 40 via shaft 42. Each zone is provided with four equally spaced vertical baffles 44 and with a horizontal baffle 46, the latter comprising an outer section 48 attached to the inner wall of reactor 30 and an intersection 50 attached to shaft 42. Between them, outer section 48 and inner section 50 define an annular area 52 of limited back-mixing. Usually, annular area 52 comprises about 2-15%, most often about 4-8%, of the inner cross-sectional area of reactor 30.

A mixture of product solution and aqueous phase is removed via line 36. The two phases are separated and polycarbonate is recovered conventionally from the organic phase; the spent base solution forming the aqueous phase may be recycled for preparation of aqueous sodium hydroxide solution to enter CSTR 2 at 12.

The invention is illustrated by the following examples.

EXAMPLE 1-5

The reactor was a 1-liter jacketed baffled vessel equipped with a dual flat blade turbine impeller, a pH probe, a thermocouple, two condensers cooled at $-18°$ C. and two addition tubes, one for phosgene and the other for aqueous sodium hydroxide solution.

The reactor was initially charged with 500 ml. of methylene chloride, a measured quantity of water and 114 grams (0.5 mole) of bisphenol A. The reactor was heated to 25°-30° C. and purged with nitrogen, and then phosgene was passed in for 20 minutes at 3.71 g./min. (0.75 mole total), with stirring at 450 rpm. At the same time, 50% aqueous sodium hydroxide solution was added to maintain the desired pH.

After phosgenation had proceeded for 20 minutes, the reactor was purged with nitrogen for 5 minutes with continued addition of aqueous sodium hydroxide solution to maintain the desired pH. The product was analyzed by high pressure liquid chromatography.

The relevant parameters and results are given in Table I. Bischloroformate and monochloroformate are respectively designated "BCF" and "MCF". "PC oligomer" designates hydroxy-terminated species. High polymer was detected only in the product of Example 3, and only in trace amounts.

TABLE I

|  | Example | | | | |
| --- | --- | --- | --- | --- | --- |
|  | 1 | 2 | 3 | 4 | 5 |
| pH | 8.0* | 8.5 | 9.0 | 9.5 | 10.0 |
| Water, ml. | 160 | 250 | 250 | 250 | 250 |
| Final vol. ratio, aq.-org. phase | 0.46 | 0.65 | 0.64 | 0.64 | 0.65 |
| Product distribution, mole %: | | | | | |
| Monomer MCF | 12.4 | 26.4 | 15.8 | 8.4 | 5.8 |
| Dimer MCF | 9.5 | 14.0 | 9.3 | 4.9 | 3.4 |
| Monomer BCF | 25.5 | 22.7 | 26.2 | 30.1 | 31.3 |
| Dimer BCF | 22.1 | 17.6 | 19.4 | 21.0 | 21.0 |
| Trimer BCF | 12.9 | 4.3 | 10.5 | 14.3 | 15.4 |
| Tetramer BCF | 5.3 | 0.8 | 5.9 | 9.6 | 10.6 |
| Pentamer BCF | 2.6 | 0.6 | 2.0 | 5.1 | 6.1 |
| Hexamer BCF | 1.3 | 0.2 | 1.1 | 3.3 | 3.9 |
| Heptamer BCF | 0.6 | 0 | 0.5 | 2.1 | 2.3 |

TABLE I-continued

|  | Example | | | | |
| --- | --- | --- | --- | --- | --- |
|  | 1 | 2 | 3 | 4 | 5 |
| PC oligomer | 7.8 | 7.4 | 2.6 | 0.4 | 0.2 |
| % COCl$_2$ hydrolyzed | 7.1 | 10.2 | 0.3 | 0.2 | 0.9 |
| Avg. degree of polymerization | 2.22 | 1.8 | 2.07 | 2.39 | 2.47 |

*Actual value higher by about 1.0-1.5.

Referring first to Example 1, it will be seen that problems in pH monitoring and control were encountered at a low volume ratio of aqueous to organic phase. This was true because the pH probe became coated with tenacious solids which distorted its reading.

From Example 2, it is evident that the proportion of monochloroformate in the product may be large at pH values below about 9. The most favorable product distributions are found in Examples 3-5, wherein the pH and volume ratio were both in the preferred range.

EXAMPLE 6

In two separate runs, a 250-ml. Morton flask was charged with 56 ml. of methylene chloride, 0.5 ml. of 50% aqueous sodium hydroxide solution, 8 ml. of water and 0.68 ml. of triethylamine. The mixture was warmed to reflux, with stirring, and 40 ml. of bischloroformate solution in methylene chloride (prepared according to Examples 1 and 4, respectively) was added over 30 minutes. There were simultaneously added 5 ml. of 50% aqueous sodium hydroxide solution over the first 25 minutes, and 0.05 ml. of triethylamine in 10 equal portions at 3-minute intervals. There were obtained the desired cyclic polycarbonate oligomer mixtures. The product from the bischloroformate composition of Example 1 contained 28.7% high polymer; that from the bischloroformate mixture of Example 4 contained 21.5% high polymer.

EXAMPLE 7

A 500-ml. Morton flask was charged with 100 ml. of the organic phase from Example 4 and 140 ml. of water. A syringe was charged with 5 ml. of a methylene chloride solution containing 485 mg. of phenol and 84 mg. of triethylamine (6.22 and 1 mole percent, respectively, based on structural units in the oligomer composition). The pH of the reaction mixture was adjusted to 12 by the addition of 50% aqueous sodium hydroxide solution, and the mixture was stirred at 400 rpm. with a paddle stirrer as the catalyst solution was metered in over 5 minutes, with continued sodium hydroxide addition to maintain the desired pH. Analysis of the reaction mixture after 20 minutes showed the formation of a linear bisphenol A polycarbonate having a weight average molecular weight of 34,000 and an intrinsic viscosity of 0.37 dl./g., as determined in chloroform at 25° C.

What is claimed is:

1. A method for preparing a linear polycarbonate which comprises the steps of:
   (A) preparing a bischloroformate oligomer composition by passing phosgene into a heterogeneous mixture consisting essentially of water, a substantially inert, substantially water-insoluble organic liquid and at least one dihydroxyaromatic compound in a tank reactor, and simultaneously introducing an aqueous alkali or alkaline earth metal base solution at a rate to maintain the aqueous phase of said mixture at a pH in the range of 8–11; the temperature of said mixture being maintained in the range of about 15°–50° C., the volume ratio of aqueous to organic phase at the conclusion of phosgenation being in the range of about 0.4–1.0:1 and the total amount of phosgene employed being at least about 1.1 mole per mole of dihydroxyaromatic compound; said mixture being agitated under conditions sufficient to prevent segregation of the aqueous and organic liquid phases;

(B) passing an interfacial polycarbonate formation catalyst into a mixture of said bischloroformate composition, water and a substantially inert, substantially water-insoluble organic liquid in a tank reactor, with effective agitation, and simultaneously introducing an aqueous alkali or alkaline earth metal base solution at a rate to maintain the aqueous phase of said mixture at a pH in the range of about 10–14, the rate of catalyst addition being adjusted to effect polycarbonate formation under controlled conditions; and (C) recovering said linear polycarbonate.

2. A method according to claim 1 wherein the interfacial polycarbonate formation catalyst is a tertiary amine, the organic liquid in steps A and B is methylene chloride and the base in steps A and B is sodium hydroxide.

3. A method according to claim 2 wherein the tertiary amine is triethylamine and the dihydroxyaromatic compound has the formula HO-$A^1$-Y-$A^2$-OH, wherein each of $A^1$ and $A^2$ is a monocyclic divalent aromatic radical and Y is a bridging radical in which one or two atoms separate $A^1$ from $A^2$.

4. A method according to claim 3 wherein unreacted phosgene is removed from the product of step A by at least one of (1) purging the reaction mixture with an inert gas and (2) continuing addition of base to hydrolyze said phosgene.

5. A method according to claim 3 wherein the dihydroxyaromatic compound is bisphenol A.

6. A method according to claim 5 wherein the pH in step B is in the range of about 11–12.5, and there is also added an effective amount of a monohydroxyaromatic compound to regulate polycarbonate molecular weight.

7. A method according to claim 5 wherein steps A and B are conducted batchwise in the same tank reactor.

8. A method according to claim 5 wherein steps A and B are conducted continuously in two continuous-flow stirred tank reactors in series, and in step A a portion of the dihydroxyaromatic compound and organic liquid are initially present and the remainder are added concurrently with the phosgene and base.

9. A method according to claim 4 wherein the reaction is conducted continuously, with step A being conducted in a continuous-flow stirred tank reactor in which a portion of the dihydroxyaromatic compound and organic liquid are initially present and the remainder are added concurrently with the phosgene and base, and step B in a second continuous-flow stirred tank reactor followed by a further reaction system operating under limited back-mixing conditions.

10. A method according to claim 9 wherein the further reaction system is a continuous-flow tubular reactor containing multiple reaction zones.

* * * * *